(12) United States Patent
Jerjomin

(10) Patent No.: US 8,062,213 B2
(45) Date of Patent: Nov. 22, 2011

(54) ENDOSCOPE WITH A DEFLECTING ELEMENT FOR FLUSHING MEDIA

(75) Inventor: Vitali Jerjomin, Tallinn (EE)

(73) Assignee: Karl Storz GmbH & Co. KG (DE)

( * ) Notice: Subject to any disclaimer, the term of this patent is extended or adjusted under 35 U.S.C. 154(b) by 938 days.

(21) Appl. No.: 11/407,734

(22) Filed: Apr. 20, 2006

(65) Prior Publication Data

US 2006/0258913 A1    Nov. 16, 2006

(30) Foreign Application Priority Data

Apr. 20, 2005  (DE) .......................... 10 2005 019 142

(51) Int. Cl.
*A61B 1/04* (2006.01)
*A61B 1/12* (2006.01)

(52) U.S. Cl. ......... 600/157; 600/127; 600/129; 600/156
(58) Field of Classification Search .................. 600/129, 600/106, 127, 175, 155–159
See application file for complete search history.

(56) References Cited

U.S. PATENT DOCUMENTS

| | | | | |
|---|---|---|---|---|
| 4,436,087 | A | | 3/1984 | Ouchi .............................. 128/6 |
| 4,881,810 | A | | 11/1989 | Hasegawa ...................... 356/241 |
| 5,536,236 | A | * | 7/1996 | Yabe et al. ..................... 600/125 |
| 5,573,494 | A | * | 11/1996 | Yabe et al. ..................... 600/121 |
| 5,630,795 | A | * | 5/1997 | Kuramoto et al. .............. 604/30 |
| 5,685,823 | A | * | 11/1997 | Ito et al. ......................... 600/127 |
| 5,746,695 | A | | 5/1998 | Yasui et al. ..................... 600/127 |
| 6,059,719 | A | * | 5/2000 | Yamamoto et al. ........... 600/127 |
| 6,176,867 | B1 | * | 1/2001 | Wright ........................... 606/184 |
| 6,409,657 | B1 | * | 6/2002 | Kawano ......................... 600/157 |
| 2002/0026097 | A1 | * | 2/2002 | Akiba ............................. 600/157 |
| 2002/0151768 | A1 | * | 10/2002 | Akiba ............................. 600/157 |
| 2005/0038317 | A1 | * | 2/2005 | Ratnakar ........................ 600/101 |

FOREIGN PATENT DOCUMENTS

| | | |
|---|---|---|
| JP | 6-14865 | 1/1994 |
| JP | 06169879 A * | 6/1994 |
| WO | WO 2006/014814 | 2/2006 |

OTHER PUBLICATIONS

European Search report; Jul. 13, 2006; 7 pages.
US 5,772,579, 06/1998, Reisdorf et al. (withdrawn)

* cited by examiner

*Primary Examiner* — Matthew J Kasztejna
*Assistant Examiner* — Ryan Henderson
(74) *Attorney, Agent, or Firm* — St. Onge Steward Johnston & Reens LLC

(57) ABSTRACT

An endoscope has a shaft having a distal end, the distal end terminates in an endoscope head having at least one light inlet and at least one channel for passing a flushing medium, the endoscope head having a body, a segment of the body being able to be detached from the body, the segment having a deflecting element arranged at a distance in front of a mouth of the at least one channel for passing the flushing medium, the deflecting element serves for guiding the flushing medium emerging the channel towards the light inlet, the segment being received captively and in a defined position on the body and being secured thereon by means of a holder.

13 Claims, 3 Drawing Sheets

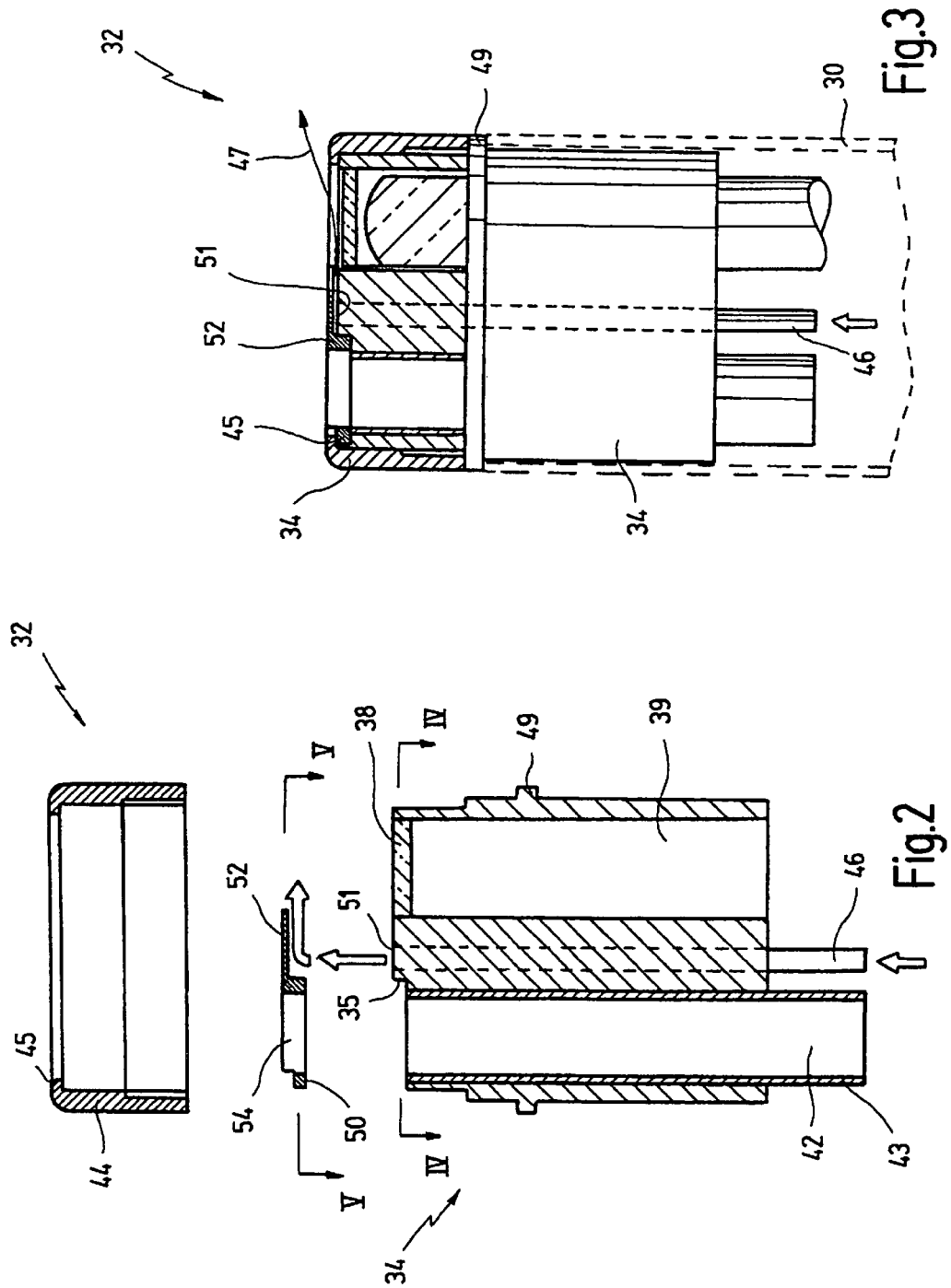

ENDOSCOPE WITH A DEFLECTING ELEMENT FOR FLUSHING MEDIA

CROSS-REFERENCE TO RELATED APPLICATIONS

The present application claims priority of German patent application No. 10 2005 019 142.8 filed on Apr. 20, 2005, the content of which is incorporated herein by reference.

BACKGROUND OF THE INVENTION

The invention relates to an endoscope, in particular a flexible video endoscope, having a shaft which, at its distal end, terminates in an endoscope head having at least one light inlet and at least one channel for passage of a flushing medium, and with a deflecting element which is arranged at a distance in front of a mouth of the channel in order to deflect the emerging flushing medium to the light inlet.

An endoscope of this kind is known from U.S. Pat. No. 4,436,087, for example.

Endoscopes of this kind are used in particular for viewing hollow organs within the body. With flexible endoscopes, it is possible, for example, to examine the trachea, the oesophagus, the stomach or the intestine.

At the distal end, a light inlet is provided through which the light of the image to be observed is introduced and then conveyed to the proximal end. In rigid endoscopes, this is done using a rod lens system; in modern flexible endoscopes, a light-sensitive chip, arranged in the distal endoscope head, converts the incoming light signals into an electrical signal and conveys this to the proximal head section. There, the electrical signal is converted again into an image signal and, for example, displayed on a monitor.

In practical application, it has now been found that the light inlet or image inlet becomes soiled and that it is necessary to clear it of contaminating material.

For this purpose, it has been proposed to provide a channel running through the shaft of the endoscope for the passage of a flushing medium, for example a gaseous or a liquid medium. Since this channel by necessity has to run alongside the optics channel, suitable measures have to be taken to deflect the flushing medium sideward and guide it across the light inlet in order to clean the latter. Numerous construction proposals have now been made for how this jet of flushing medium can be deflected.

In the aforementioned U.S. Pat. No. 4,436,087, this is achieved by a cap being fitted, in most cases screwed, onto the distal end of the endoscope head, with a deflecting element projecting radially inwards from the inner side of said cap.

In this case, the deflecting element is configured such that it comes to lie at a slight distance in front of the mouth of the channel from which the flushing medium emerges. The emerging flushing medium then hits the deflecting element, is diverted sideward by the latter from the axial direction to a radial direction, and the jet of flushing medium is guided across the light inlet in order to flush or blow it clear.

Certain disadvantages of this construction have been found in practical application.

The inner cavity of the cap proved to be a kind of dirt trap and tends to cause more soiling of the light inlet than is the case in an endoscope without such a cap.

To clean a flushing channel, for example by a cleaning brush being guided through it in the axial direction, the cap has to be taken off, since otherwise the brush would strike against the deflecting element. Bearing in mind that endoscopes have a diameter in the range of a few millimeters, it is evident that the components involved here are relatively small and sensitive.

A further disadvantage is that the fitted closure cap finally has to be positioned very exactly with respect to the deflecting element to ensure that the desired deflection result can be achieved.

It is customary for several channels to be routed through the shaft of an endoscope, that is to say not just the channel for the optics and a flushing channel, but in most cases also one or more channels for guiding the illumination light, and often also an instrument channel for guiding an instrument through the shaft.

To allow the light inlet to be flushed clear or blown clear in the desired manner, the deflecting element then has to come to lie in a very specific position over the mouth of the flushing channel so that the jet is in fact guided across the light inlet and not across the instrument channel. At the same time, the deflecting element has to be so small that it does not impede the entry of light into the light inlet and does not screen off the illumination light or even block the instrument channel. That is to say, the deflecting element projects from an inner circumferential face of the cap within a relatively small area.

If the cap is now screwed on too little or too far, the deflecting element does not come to lie in its exactly predetermined position, and the desired flushing result is not achieved.

From U.S. Pat. No. 5,746,695 an endoscope of the above mentioned kind is known having a closing cap comprising the deflecting element as an integral part for deflecting the emerging flushing medium laterally towards the light inlet. Contrary to the above mentioned construction with a cap which can be screwed on, the cap is contoured in a manner that it can be placed only in a particular orientation on the distal end of the endoscope. For it, both the distal end of the endoscope head and the cap are provided with respective complementary projections and recesses respectively for assuring a correct positioning of the cap together with the deflecting element.

The disadvantage of that construction is that both the distal end of the endoscope head and the corresponding face of the cap are designed very complicated. This needs an expensive machining of these parts. Further, the numerous recesses and undercuts provide bacteria niches and therefore need very deep cleaning and sterilization processes.

It is an object of the present invention to provide simple construction measures that guarantee an exact positioning of the deflecting element so that it is possible to achieve an exactly oriented jet of flushing medium even after several dismantling, cleaning and assembling procedures.

SUMMARY OF THE INVENTION

According to the invention this object is achieved by an endoscope comprising a shaft having a distal end, said distal end terminates in an endoscope head having at least one light inlet and at least one channel for passing a flushing medium, said endoscope head having a body, a segment of said body being able to be detached from said body, said segment having a deflecting element arranged at a distance in front of a mouth of said at least one channel for passing said flushing medium, said deflecting element serves for guiding said flushing medium emerging said channel towards said at least one light inlet, said segment being received captively and in a defined position on said body and being secured thereon by means of a holder.

A segment within the meaning of the present invention is understood as a piece of the mostly approximately cylindrical body of the endoscope head that can be detached from the latter. It is possible to imagine this as being like removing a brick as a segment from a wall made of bricks.

The actual deflecting element is arranged on this segment. By virtue of the configuration as segment, the latter can be placed with an exact fit into the corresponding gap in the body of the endoscope head. This has the result of ensuring an exact orientation of the deflecting element protruding from the segment, so that this deflecting element is in an exact orientation each time the segment has been removed for cleaning the flushing channel and has then been put back in place. The fitting of the segment onto the body of the endoscope head can be done only in a single exactly aligned position and is therefore no longer dependent on the skill or attention of the person assembling the endoscope head after a cleaning procedure. An incorrect position caused by a cap being screwed on too little or too far is therefore ruled out by the system.

It is thus possible to achieve a permanently uniform fit and uniform orientation of the deflecting element, even if such an endoscope has undergone numerous cleaning cycles.

After the segment has been fitted in place, it is held securely and captively by the holder. This holder serves only to hold the segment and has no influence on the orientation of the deflecting element. Therefore, it is possible, for example, to design this holder as a screw cap.

In a further embodiment of the invention, the segment is magnetic and can be held magnetically on the body.

This measure has the advantage that the dismantling and assembly are made very much easier.

For the dismantling procedure, it is possible first to remove the holder, for example the aforementioned screw cap. The magnetic holder guarantees that the segment does not fall off the body of the endoscope. To remove it, it has to be gripped by hand or with a tool. Similarly, after a cleaning and sterilizing procedure, assembly is then also made easier. Because of the magnet effect, the segment is held on the body of the endoscope head until it is secured captively by a corresponding holder.

The segment can be put into position, the correct fit can be checked for, and a clip connection can then be closed by pressing it in, for example.

In a further embodiment of the invention, the segment has approximately the shape of a portion of a circle, from which the deflecting element protrudes.

This measure has, among other things, the advantage that, even with this relatively small component part, a relatively stable body is formed, for example in the shape of a portion of a disc, which body, at the time of assembly, is easily fitted onto the corresponding cutout in the body. The actual deflecting element then protrudes from the body, or the body itself can then be designed as part of the deflecting element.

In a further embodiment of the invention, when a plurality of channels are provided for passage of flushing media, a plurality of deflecting elements are correspondingly present on the segment.

This measure has the advantage that, if, for example, a first channel is provided for the delivery of a liquid medium, for example flushing water, and a second channel is provided for the delivery of a gaseous medium, the light inlet can be acted on first by the liquid flushing medium. Said light inlet is provided with a deflecting element suitably arranged above the mouth of this channel. Moreover, on a channel arranged laterally from this and used for the delivery of flushing air, a corresponding further deflecting element is provided so as then to be able to guide the air across the light inlet for the purpose of final flushing and drying. It is possible to provide these several deflecting elements as one integral deflecting element on the segment, such that a certain area in each case comes to lie over an opening of a mouth of one of the two flushing channels.

In a further embodiment of the invention, at least one opening for a further channel, in particular an instrument channel, is cut out in the segment.

This measure has the advantage that the segment can represent a relatively large area of the end of the body of the endoscope head, for example a half disc or more, and as a result is then relatively stable. It is then possible to cut a continuous opening through the body, for example in order to keep free an instrument channel lying in this area. This contributes to the stability of the segment and makes it possible to design the latter as a relatively large component part, which is then accordingly easy to handle.

In a further embodiment of the invention, the deflecting element is designed in such a way that it directs the flushing medium not only to a light inlet, but also to an illumination light outlet or, if appropriate, to several such outlets.

The main aim is to flush clear the light inlet, in order to achieve an optimal viewing result. Sometimes, however, the light efficiency is reduced by the light outlet opening for the illumination light becoming covered by contaminating material and as a result becoming dimmed. By means of the construction measure now proposed, it is possible to flush clear, or blow clear, not just the light inlet, but also the illumination light outlets.

In a further embodiment of the invention, on the distal face of the body of the endoscope head, between a channel for guiding a flushing medium and the inlet or outlet to be flushed, a channel-like recess is in each case cut out for guiding the flushing medium.

This measure has the advantage of permitting targeted guidance of the flushing medium from the mouth of the channel to the inlet or outlet that is to be flushed. The deflecting element, which comes to lie over the channel-like recesses, constitutes a kind of lid for these shaft-like or channel-like recesses, so that as a whole a guide channel for the flushing medium is created.

Depending on the configuration of these channel-like recesses, the flushing medium is guided from a channel, or from its mouth, in a targeted manner to one or more inlets or outlets for the light-conveying means.

This measure has the advantage of permitting particularly targeted guidance of the flushing media. The channel-like recesses are to be produced during the original manufacture of the body, which, for example, can be manufactured as an injection-moulded part.

It will be appreciated that the aforementioned features and those still to be explained below can be used not only in the cited combinations, but also in other combinations or singly, without departing from the scope of the present invention.

BRIEF DESCRIPTION OF THE DRAWINGS

The invention is described and explained in more detail below on the basis of a selected illustrative embodiment and with reference to the attached drawings, in which:

FIG. 2 shows an exploded view of the main components of the distal endoscope head, FIG. 3 shows the endoscope head in the assembled state, with the optics inserted.

In FIG. 1, a flexible endoscope according to the invention is designated in its entirety by reference number 10.

DETAILED DESCRIPTION OF THE INVENTION

Figure 1:
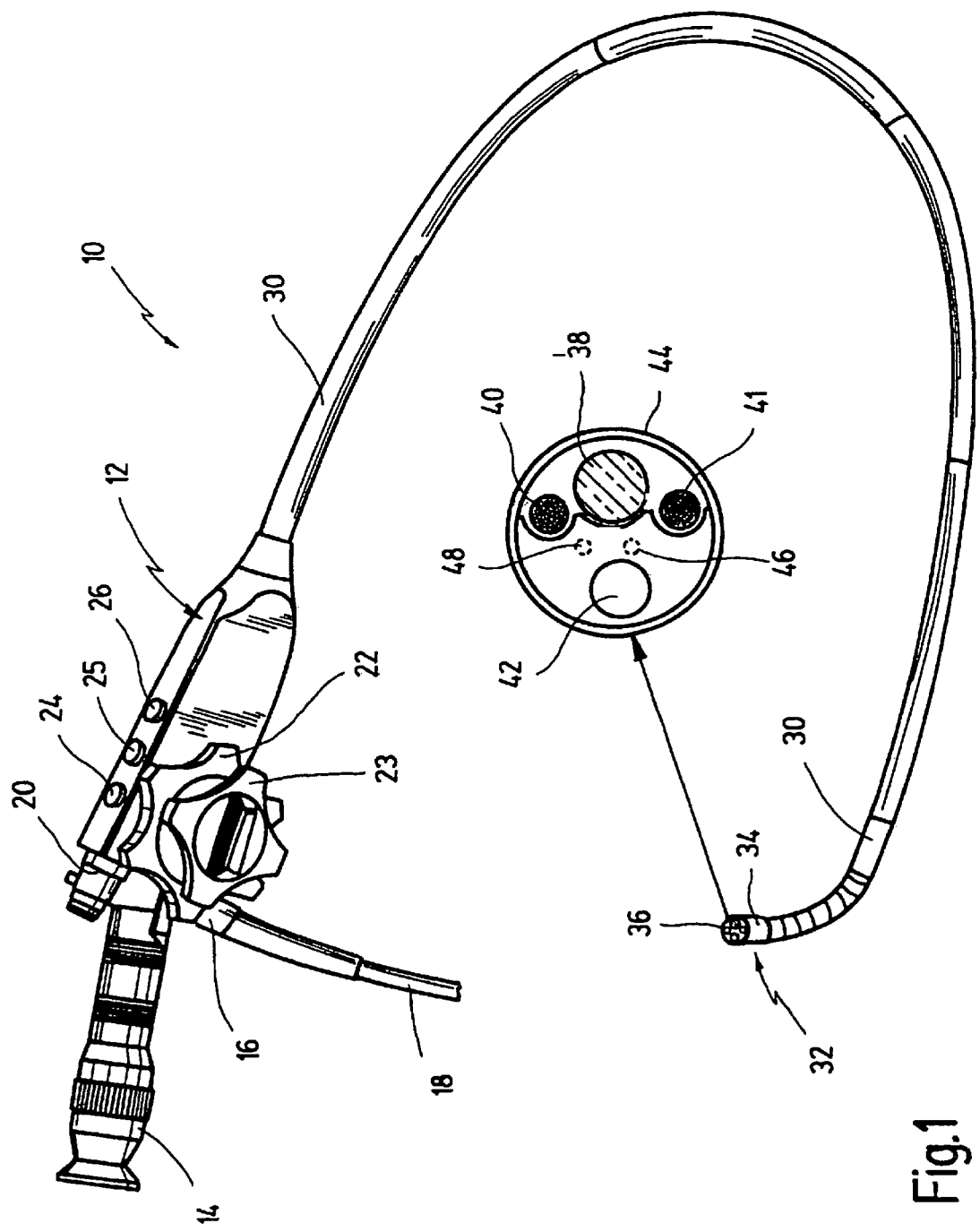
FIG. 1 shows an endoscope, namely a flexible video endoscope, provided with an endoscope head according to the invention with a deflecting element, a slightly enlarged plan view of the distal end being shown in the centre of the figure.

The flexible endoscope 10 has, at its proximal end, a head section designated overall by reference number 12. An eyepiece 14 extends from the proximal face of the head section 12. A laterally extending connector piece 16 is used for connection of a cable 18 which can include lines for lighting, flushing, insufflation, suction, image transmission and the like. A further connector piece 20 extending approximately in the direction of the eyepiece 14 is provided so that instruments, for example forceps, coils or the like, can be pushed through it into the endoscope 10 or the head section 12.

Two hand-operated wheels 22, 23 arranged laterally on the head section 12 can be used to adjust the viewing direction of the endoscope. Also provided in the area of the head section 12 are switches 24, 25, 26 via which various functions, for example suction, flushing or the like, can be controlled, as is known per se in the design of flexible endoscopes.

An elongate, flexible shaft 30, in the present illustrative embodiment with a length of approximately one meter, extends from the head section 12. The shaft 30 is made of a flexible plastic material that permits curving and bending of the shaft 30.

The end of the shaft 30 is closed by an endoscope head 32. It will be seen from the enlarged view of the distal end face that a light inlet 38 opens out here, through which light can pass into the interior of the shaft 30.

This light corresponds to the image that can be observed through the eyepiece 14. Depending on the design of the endoscope, the light is conveyed from the light inlet 38 via light guides, either a rigid lens system, or, in the case of a flexible endoscope, a flexible light guide. In the design as a video endoscope, the incident light is converted by a CCD chip into an electrical signal and is then delivered via the cable 18 to a monitor or to an image-processing system.

It will also be seen that two illumination light outlets 40, 41 are present through which illumination light is delivered to the distal end and emerges from the latter.

It will also be noted that a continuous instrument channel 42 is provided.

An instrument pushed in through the connector piece 20 can emerge at the distal end by way of this instrument channel 42.

Two channels 46 and 48 are indicated by dot-and-dash lines, the channel 46 being an air channel for delivery of flushing air, and the channel 48 being designed as a water-conveying channel for delivering water as flushing liquid to the distal end.

As will be apparent from FIG. 1, these channels 46 and 48 lie hidden under a component part that will first be described in detail in connection with FIGS. 2 to 6.

From the exploded view in FIG. 2, it will be seen that the endoscope head 32 has an approximately cylindrical body 34.

It will also be seen from this exploded view that a segment 50 can be detached from the distal end area of the body 34 and that a deflecting element 52 projects from the side of the segment.

When it is placed onto the top face of the body 34, the segment 50 is secured by means of an annular cap 44 being screwed on, as can be seen from FIG. 3. For this purpose, the annular cap 44 has a corresponding annular flange 45 which engages over part of the circumference of the segment 50. The annular cap 44 serves for holding the segment 50 of the body 34.

Figure 5:
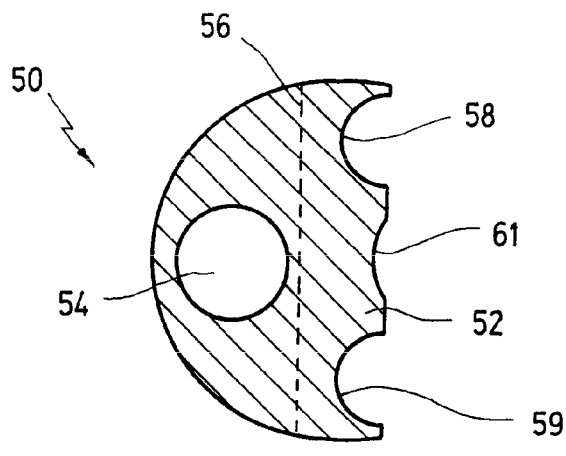
FIG. 5 shows a cross section along the line V from FIG. 2.

From the cross-sectional view in FIG. 5, in connection with the view in FIG. 2, it will be seen that the segment 50 has a body in the shape of a portion of a circle which, in the view shown in FIG. 5, extends to the left from the broken line. A corresponding step 35 is formed on the top face of the body 34, and this portion of the segment can be placed with a complementary fit on this step.

To ensure that the instrument channel 42 reaches right to the end, a corresponding opening 54 is formed in the segment 50.

The portion extending to the right from the broken line 56 in FIG. 5 contains the actual deflecting element 52. In this area, two semicircular recesses 58 and 59 are cut out, and also a further curved recess 61.

Figure 6:
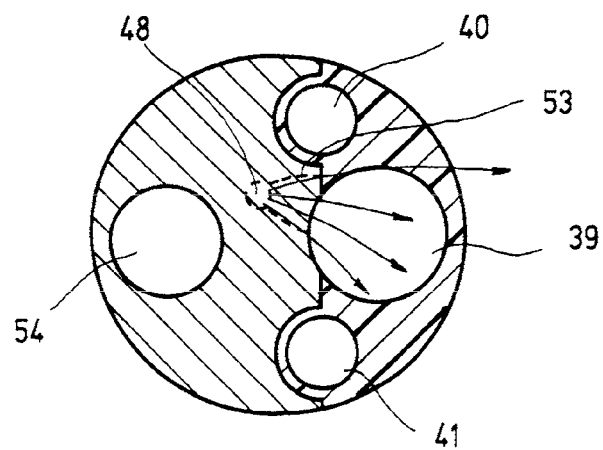
FIG. 6 shows a cross section which corresponds to the cross section in FIG. 4 and in which the segment shown in FIG. 5 is fitted in place.

When the segment 50 is placed on the distal end of the body 34, as can be seen for example in FIG. 6 and FIG. 3, the semicircular recesses 58, 59 and 61 fit neatly round the contour of the illumination light outlets 40 and 41 and round the light inlet or optics channel 39.

Figure 4:
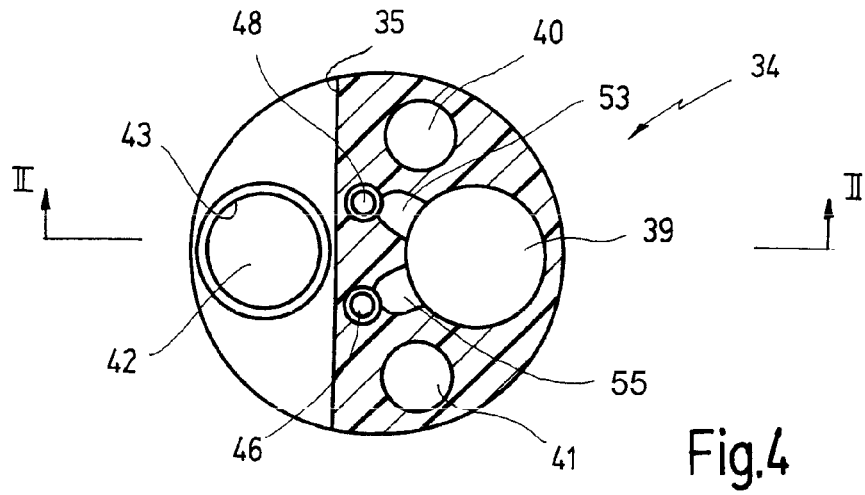
FIG. 4 shows a cross section along the line IV-IV from FIG. 2.

It will be seen from FIG. 4 that the two flushing channels, namely the air channel 46 and the water channel 48, run approximately centrally through the body 34, these channels being enclosed by metal tubes fitted into the body 34, which itself is made of plastic.

As will be seen from the cross-sectional views in FIG. 2 and FIG. 3, a corresponding metal tube piece 43 is inserted into the instrument channel 42.

The segment 50 is either itself made of magnetic material or is provided with a magnetic insert such that it fastens magnetically to the top face of the body 34.

In this state, the underside of the deflecting element 52 comes to lie at a slight distance, for example two tenths of a millimeter, above the mouth 51 of the flushing channels 46 and 48. If air is now passed through the channel 46, as is indicated by an arrow in FIG. 2, the air emerging from the mouth 51 of this channel 46 hits the underside of the deflecting element 52 and is deflected sideward by the latter in the direction of the light inlet 38 or the optics channel 39, as is indicated by arrows in FIG. 2, by the arrow 47 in FIG. 3, and by the flow arrows in FIG. 6.

From the cross-sectional view in FIG. 4, it will be seen that, in the area between the channel 46 and the optics channel 39, a channel-like recess 55 is present on the top face or end face of the body 34. Similarly, a corresponding channel-like recess 53 is provided between the channel 48 and the optics channel 39. These recesses 53 and 55 ensure that the flushing medium emerging from the channels 46 and 48 is correctly targeted at the optics channel 39. The deflecting element 52 covers these distally open recesses 53 and 55, as can be seen from the view in FIG. 6. With the segment 50 in place, precisely defined flow channels and connection channels are thus provided between the channels 46 and 48 for delivering the flushing medium into the optics channel 39 that is to be flushed. In this configuration, the optics channel 39 can be flushed alternately with air or with water.

By means of a suitably different configuration or orientation of these channels, the illumination light outlets 40 and 41 can also be flushed.

As will be seen in particular from FIG. 6, the deflecting element 52 extends in such a way that, for example, flushing liquid emerging from the channel 48 is guided not just across the optics channel 39 but also across the corresponding illumination light outlet 40, such that the latter is at the same time also flushed clear of contaminants. The same applies then for the air channel 46.

For cleaning or sterilizing, the annular cap 44 is unscrewed, as can be seen for example from the exploded view in FIG. 2, but the magnetic force ensures that the segment 50 at first remains in place. It can then be removed, such that the channels 46 and 48 can then be cleaned, for example by means of brushes being pushed through them.

After the cleaning and sterilizing, the segment 50 is placed back on the top face of the body 34, this being made easier by the fact that it can be pushed from above and from the side onto the edge 35. This part is then exactly centred and fixed by means of the annular cap 44 being screwed on. A corresponding inner thread (not shown) of the annular cap 44 engages in a corresponding outer thread on the body 34.

An annular flange 49 extending round the body 34 limits this movement. On the opposite side, this annular flange 49 limits the depth of insertion of the endoscope head 32 into the shaft 30.

What is claimed is:

1. An endoscope comprising:
    a shaft having a distal end, said distal end terminating in an endoscope head having at least one light inlet and at least one channel for passing a flushing medium,
    said endoscope head having a body,
    a segment located at the distal end of said body, said segment having a deflecting element, said deflecting element serving for guiding said flushing medium emerging from said channel towards said at least one light inlet,
    said segment being loosely put in a defined position directly on an outer surface of said distal end of said body and being secured thereon by means of a holder, said holder covering at least partially said segment, wherein said segment is a separate part held between said holder and said body, said segment being placed with an exact fit into a corresponding gap in said body, said fit can be done only in a single exactly aligned position in said gap,
    said segment being maintained directly on the outer surface of the distal end of said shaft, where said segment does not protrude within the at least one channel for passing said flushing medium, and
    said holder surrounds and extends beyond the distal end of the body.

2. The endoscope of claim 1, wherein said segment is magnetic and can be held magnetically on said body.

3. The endoscope of claim 1, wherein said segment has approximately a shape of a portion of a circle, from which said deflecting element protrudes.

4. The endoscope of claim 1, wherein a plurality of channels for passing a flushing media are provided, said segment having a respective plurality of deflecting elements for deflecting flushing media emerging from said plurality of channels.

5. The endoscope of claim 1, wherein at least a further channel is provided in that body of said endoscope head, said further channel opens in said body, a corresponding opening being cut out in said segment, said opening corresponds to a mouth of said further channel.

6. The endoscope of claim 5, wherein said further channel is an instrument channel.

7. The endoscope of claim 1, wherein said head of said endoscope has at least one illumination light outlet, said deflecting element of said segment is designed in such way, that said flushing medium being deflected to said at least one illumination light outlet, too.

8. The endoscope of claim 1, wherein a channel-like recess is cut out in a distal end face of said body, said channel-like recesses extended between said channel and said light inlet for guiding said flushing medium.

9. The endoscope of claim 8, wherein said deflecting element of said segment covers said channel-like recess.

10. The endoscope of claim 1, wherein a channel-like recess is cut out in a distal end face of said body, said channel-like recess extended between said channel and an illumination light outlet for guiding said flushing medium.

11. The endoscope of claim 10, wherein said deflecting element of said segment covers said channel-like recess.

12. The endoscope of claim 1, wherein said holder is designed as a cap which can be placed on said body and said segment.

13. The endoscope of claim 1, wherein said segment has the shape of an irregular disc.

* * * * *